United States Patent [19]

Miller

[11] Patent Number: 4,724,217
[45] Date of Patent: Feb. 9, 1988

[54] ULTRATRACE ANALYSIS OF TRANSURANIC ACTINIDES BY LASER-INDUCED FLUORESCENCE

[75] Inventor: Steven M. Miller, Chelmsford, Mass.

[73] Assignee: The United States of America as represented by the United States Department of Energy, Washington, D.C.

[21] Appl. No.: 842,764

[22] Filed: Mar. 21, 1986

Related U.S. Application Data

[63] Continuation of Ser. No. 547,280, Oct. 31, 1983, abandoned.

[51] Int. Cl.$^4$ ............................................. G01N 21/64
[52] U.S. Cl. ................................... 436/82; 250/458.1; 250/459.1; 436/172; 436/174
[58] Field of Search .................. 436/82, 155, 172, 174, 436/175, 177; 250/458.1, 459.1

[56] References Cited

U.S. PATENT DOCUMENTS

3,936,633  2/1976  DeKalb et al. ........................ 378/45
4,007,009  2/1977  Wright .............................. 250/458.1

OTHER PUBLICATIONS

Spectroscopic System for the Study of Fluorescent Lanthanide Probe Ions in Solids, Miller et al., Anal, Chem, vol. 49, No. 11 Sep. 77.
Trace Analysis of Nonfluorescent Ions by Associative Clustering with a Fluorescent Probe, Johnston et al., Anal. Chem., vol. 51, No. 11, 79.
Ultratrace Inorganic Ion Determination by Laser Exicted Fluorescence, Wright et al., Anal. Chem, vol. 50, No. 12, 78.
Book: Chemical Analysis, vol. 23 of a Series edited by Elving et al., The Formation and Properties of Precipitates, by Walton 1967 by Inter Science Publishers pp. 79–113.
A Monitor for Detecting Nuclear Waste Leakage in a Subsurface Repository, Klainer et al., 1980 in Annual Report to Dept. of Energy.
Miller, Chemical Abstract 99(8):63468y, 1963.

*Primary Examiner*—Barry S. Richman
*Assistant Examiner*—Robert J. Hill, Jr.
*Attorney, Agent, or Firm*—Henry P. Sartorio; L. E. Carnahan; Judson R. Hightower

[57] ABSTRACT

Ultratrace quantities of transuranic actinides are detected indirectly by their effect on the fluorescent emissions of a preselected fluorescent species. Transuranic actinides in a sample are coprecipitated with a host lattice material containing at least one preselected fluorescent species. The actinide either quenches or enhances the laser-induced fluorescence of the preselected fluorescent species. The degree of enhancement or quenching is quantitatively related to the concentration of actinide in the sample.

18 Claims, 3 Drawing Figures

ULTRATRACE ANALYSIS OF TRANSURANIC ACTINIDES BY LASER-INDUCED FLUORESCENCE

BACKGROUND OF THE INVENTION

The U.S. Government has rights in this invention pursuant to Contract No. W-7405-ENG-48 between the U.S. Department of Energy and the University of California, for the operation of Lawrence Livermore National Laboratory.

This is a continuation of application Ser. No. 547,280 filed Oct. 31, 1983, now abandoned.

The invention relates generally to trace analysis of transuranic actinides and, more particularly, to detection of nanogram quantities of weakly fluorescing transuranic actinides by co-precipitating samples with preselected compounds and examining the laser-induced fluorescence of the resultant crystal.

Actinide pollution poses a serious threat to public health. Because of radioactivity and toxicity, great care must be taken to contain and to monitor the spread of actinides whenever they are used in or occur as by-products of industrial processes.

Trace analysis of actinides is crucial in a variety of industrial, ecological, and public health settings. These include monitoring of ground water near nuclear waste repositories and nuclear power plants, monitoring actinide mobility under a variety of environmental conditions, monitoring the leaching of actinides immobilized in special solid matrices in preparation for waste storage, and the monitoring of actinide recovery from oceanic and terrestrial mining operations.

There are many methods of trace analysis that are applicable to the detection of actinides. Of these x-ray fluorescence analysis, neutron activation analysis, alpha spectroscopy, and optical fluorescence analysis are the most important and most sensitive. The advantages of x-ray fluorescence include direct analysis with little preparation, short analysis time (in minutes), and simple spectral interpretation. The main disadvantages of x-ray fluorescence are the safety hazards associated with an x-ray source and limited sensitivity. For example, direct analysis via x-ray fluorescence provides a sensitivity to uranium to only a parts-per-million range. DeKalb, et al., U.S. Pat. No. 3,936,633 teaches an x-ray fluorescence-based method of detecting lanthanides in a transition element host.

Neutron activation is one of the most sensitive of modern analytical techniques. Its analytical method involves exciting the nuclei of trace elements by neutron bombardment. Then, either detection of the neutron energy spectrum from the sample via pulse height analysis is performed at the time of irradiation or examination of the energy spectrum of gamma photons emitted sometime after irradiation has taken place is performed. These energy spectra are very specific to the excited nuclei that create them. For uranium, the detection limit is in the parts per billion range at 0.1 ng/ml. Although relatively sensitive, the main disadvantage of neutron activation is the necessity for high neutron fluxes requiring large accelerators or cyclotrons.

For the detection of actinides with significantly higher activities than uranium 238, alpha spectroscopy is by far the most sensitive technique. Detection limits for alpha counting analysis are typically femtocuries/liter or, for example, $10^{-2}$ parts per quadrillion for $^{239}Pu$. This is the sensitivity required to detect the plutonium background in the environment. However, such a detection limit is only obtainable with a minimum sample volume of 10 liters, a minimum counting period of three days, a signal-to-noise ratio of only 1:1, and thorough removal of interferring alpha emitters, such as $^{241}Am$, $^{232}U$, and $^{249}Bk$, before counting.

Wright and his co-workers have pioneered the use of optical fluorescent analysis of trace quantities of selected ions, particularly lanthanide ions (Wright, U.S. Pat. No. 4,007,009 "Chemical Analysis of Ions Incorporated in Lattices Using Coherent Excitation Sources"; Miller, et al., "Spectroscopic System for the Study of Fluorescent Lanthanide Probe Ions in Solid", Anal. Chem., Vol. 49, pp. 1474–1482; Wright and Gustafson, "Ultratrace Inorganic Ion Determination by Laser Excited Fluorescence", Anal. Chem., Vol. 50, pp. 1147A–1160A; Johnston and Wright, "Trace Analysis of Nonfluorescent Ions by Associative Clustering with a Fluorescent Probe", Anal. Chem., Vol. 51, pp. 1774–1780). Their technique requires the coprecipitation of the unknown ion into some preselected host lattice (or the coprecipitation of the unknown ion and a preselected fluorescent probe ion, if the unknown ion is nonfluorescent). The spectrum of the fluorescent species in the precipitate is affected by the local structure of the crystal. Typically, the fluorescent species can occupy many different sites in the crystal, each having a different effect on its release or transfer of excitation energy. The fluorescent intensity from particular sites can be related to the concentration of the unknown ion in the original solution before coprecipitation. Fluorescent species at particular sites can be chosen for analysis by selectively exciting the species at a wavelength corresponding to the absorption frequency characteristic of the site. Sites must be chosen so that there is minimum energy transfer between adjacent species in the lattice, and host materials must be chosen which do not quench fluorescence.

The foregoing illustrates the limitations of the current technology. It would be advantageous to provide an alternative to available methods, particularly in regards to ultratrace analysis of weakly fluorescing transuranic actinides.

SUMMARY OF THE INVENTION

It is therefore an object of the invention to provide a rapid method for ultratrace analysis of transuranic actinides.

Another object of the invention is to provide a rapid method for ultratrace analysis of transuranic actinides dissolved in natural and industrial fluids, such as ground water, seawater, ore leachings, extractions from soil samples, and the like.

A further object of the invention is to provide a method for fluorescence-based ultratrace analysis of weakly fluorescing or nonfluorescing transuranic actinides.

Still another object of the invention is to provide a rapid method for detecting plutonium or americium at nanogram-per-milliliter concentrations.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

These and other objects are attained in accordance with the present invention wherein, generally, a preselected host material is prepared by coprecipitating host precursor materials with the actinide-containing sample to form a precipitate; the precipitate is then preferably calcined to form a calcined precipitate. Next, the calcined precipitate is illuminated by laser light of a preselected wavelength; and the fluorescence output of a fluorescent component species within the calcined precipitate (other than the actinide itself) is related to the concentration of actinide in the original sample. Alterations in the fluorescent output of the fluorescent component species is detected by comparing fluorescent output of the actinide containing sample with those of one or more standards each comprising identically prepared preselected host material with known concentrations of the actinide of interest.

Suitable materials for the host lattice (the predominant composition of the preselected host material) include most ionic crystalline solids, but ionic crystalline solids with melting points above about 500° C. are preferred, and such ionic crystalline solids which are insoluble or slightly soluble in water, which have high molecular mass components, and which are substantially transparent to the fluorescent signals and illumination beam are most preferred.

Among these, terbium fluoride, $TbF_3$, is particularly preferred because the component species, terbium, is itself strongly fluorescent and because there exists a high rate of excitation energy migration between terbium ions. As will be discussed more fully below, the latter property is of particular advantage in the detection of plutonium. Some of the other host lattice materials listed above are weakly or nonfluorescent at convenient wavelengths. Their use in accordance with the invention requires the incorporation of a fluorescent component species as an impurity within the crystal matrix. Such a fluorescent component species is chosen from among the lanthanides, transition metals, or uranium compounds, such as uranyl, or the like.

The present invention is directed to problems associated with ultratrace analysis of weakly fluorescing transuranic actinides. It advantageously overcomes many of these problems by coprecipitating the transuranic actinides with host precursor materials to form a preselected host material in which the weakly fluorescing actinide acts as either a sensitizer or a quenching agent to a fluorescent component species within the preselected host material. In particular, the invention allows rapid ultratrace detection of plutonium ions at intra-host concentrations as low as 10 parts per million and of americium ions at intra-host concentrations as low as 1 part per million.

BRIEF DESCRIPTION OF THE DRAWINGS

The accompanying drawings, which are incorporated and form a part of the specification, illustrate equipment used in one embodiment of the invention and, together with the description, serve to explain the principles of the invention.

DETAILED DESCRIPTION OF THE INVENTION

Figure 1:
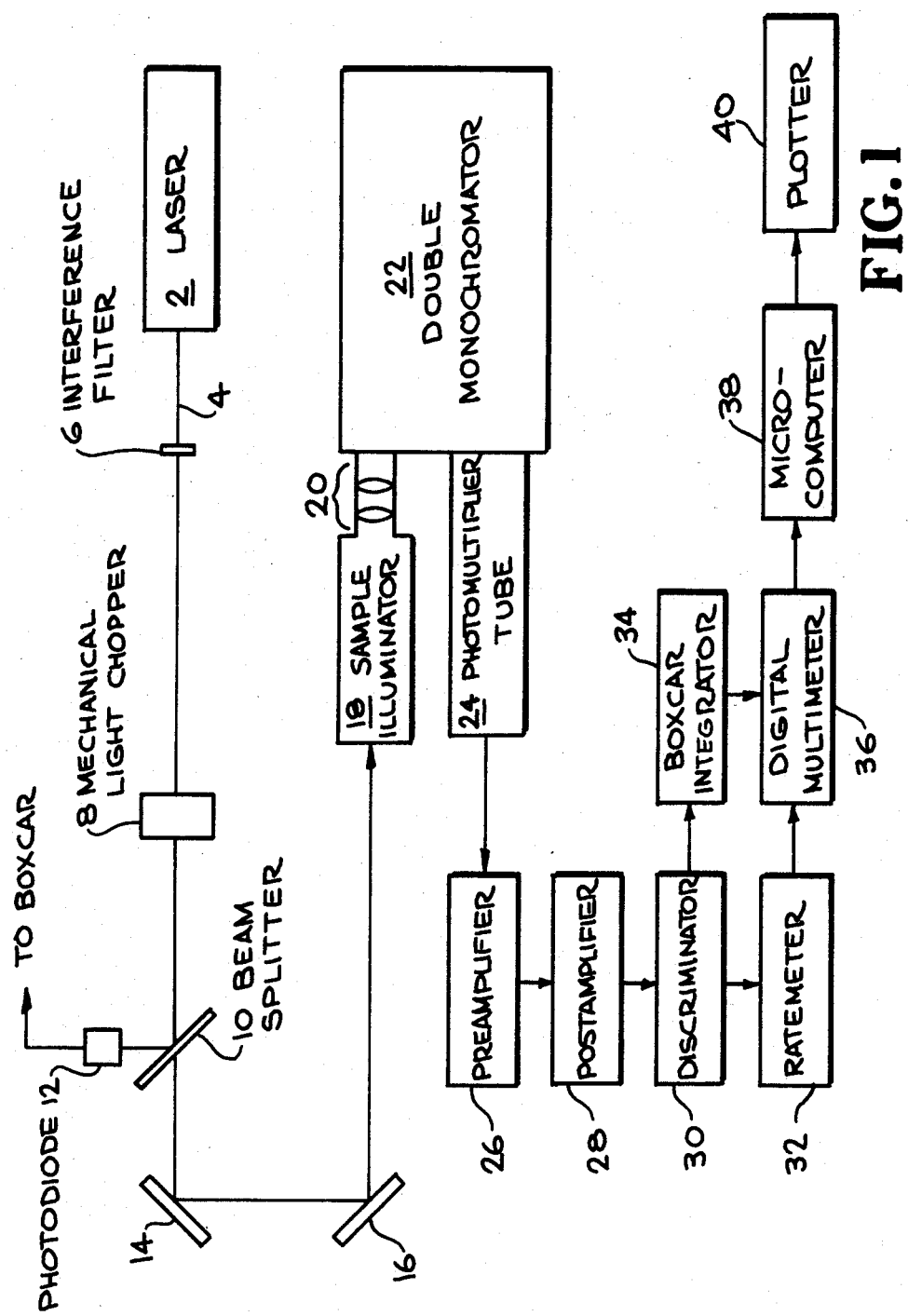
FIG. 1 diagrammatically illustrates one embodiment of an apparatus for illuminating the calcined preselected host materials and standards, and for analyzing the resultant fluorescence in accordance with the practice of the invention.

In accordance with the present invention a method is provided for detecting trace quantities of transuranic actinides in solution. A sample suspected of containing a particular actinide is mixed with host precursor materials, specifically selected for the particular actinide. Conditions are maintained which allow coprecipitation of the host precursor materials and the actinide of interest. The resulting coprecipitate is calcined to remove organic impurities and to promote crystal rearrangements into more homogeneous lower energy configurations. Finally, the calcined coprecipitate is illuminated by laser light at a preselected wavelength corresponding to the absorption band of either a fluorescent component species of the preselected host material (e.g., as in the plutonium detection method described below wherein the actinide acts as a quenching agent) or the actinide itself (e.g., as in the americium detection method described below wherein the actinide acts as a sensitizing agent). The concentration of the actinide of interest in the sample is determined by examining the differences in fluorescent output between the calcined precipitate and identically prepared standards with known concentrations of the actinide (and, in some cases, with known concentrations of interfering impurities known to be present in the sample).

The choice of the preselected host material is crucial to the invention. The invention is particularly directed to ultratrace analysis of weakly or nonfluorescing transuranic actinides. In accordance with the invention, this class of actinides is detected indirectly by fluorescence quenching or fluorescence sensitization of a fluorescent component species within the preselected host material. For sensitization or quenching to occur the fluorescent component species must possess near resonant energy levels to the actinide. Further preferences in the choice of host material include: (1) that at least one component species within the preselected host material have similar ionic radius and identical valence state to the actinide, thereby promoting selective precipitation of the actinide over other impurities during the coprecipitation step; and (2), in the case of detection by sensitization of a fluorescent component species, that the actinide have an absorption line (i) that is absent in the fluorescent component species, (ii) that is higher than the level at which resonant energy transfer takes place, and (iii) that is susceptible of non-radiative decay to the transfer level.

A. Coprecipitation

Coprecipitation is the process by which ions present in solution in small quantities can be taken out of solution via ion exchange or adsorption onto a component present in large quantities and precipitating out of solution. There are three kinetic processes which describe coprecipitation, transport through the solution, ion exchange with the surface of microcrystal and diffusion through the solid.

The effect of these processes on the incorporation of an impurity, or microcomponent, into a coprecipitate is described in Chapter 3 of Walton, *The Formation and Properties of Precipitates* (John Wiley G. Sons, New York, 1967). Accordingly, Chapter 3 of this book is incorporated by reference as a guide to choosing host precursor materials which will promote co-precipitation of the actinide of interest. The distribution coefficient of a coprecipitating system is a measure of how readily an impurity ion (i.e., the microcomponent of the system, in this case an actinide) is incorporated into the macrocomponent (i.e., the preselected host material) of the coprecipitate. The larger the distribution coefficient of the microcomponent-macrocomponent system the more readily the microcomponent is incorporated into the coprecipitate.

Large distribution coefficients result when the microcomponent ions are as similar as possible to the macrocomponent ions. Listing from the most important factors to the least important, the actinide and predetermined component species microcomponent ions should possess similar ionic radius, equal valence states and the same lattice structure as the host lattice components. The aim of these requirements is to reduce the excess free energy required to incorporate the coprecipitate into the lattice structure, thereby increasing the distribution coefficient. Less distortion is created in the lattice when exchange ions are of similar ionic radius. Similar lattice structure also reduces strains in the local crystal. Equal valences avoid the need for vacancies and interstitials required for charge compensation. Each of these exchange ion similarities keep the free energy of the crystal low and thus the distribution coefficient high. Preferably, host lattice materials are chosen for which the host lattice-actinide and host lattice-predetermined component species distribution coefficients are high.

Another factor which affects the degree of incorporation of a microcomponent is the rate of precipitation. During very fast precipitation no equilibrium is established in the kinetic processes, and the incorporation process is controlled by diffusion of ions from solution. For similar ions with similar diffusion rates incorporation is not selective; neither enrichment nor depletion of competing microcomponent ions take place as could occur under very slow precipitation rates where near-equilibrium conditions exist. Consequently, the choice of host precursor materials and conditions that promote slow precipitation are preferred; however, slow precipitation is not crucial to the invention.

A very wide range of ionic crystalline solids provides suitable host lattices. Ionic crystalline solids with melting points above about 500° C. are preferred. Representative of the materials which can be used to form the host lattice are $SrSO_4$, $PbSO_4$, $Pb_3(AsO_4)_2$, $Ba_3(AsO_4)$, $Na_2SO_4$, $NaCl$, $BaF_2$, $CaF_2$, $BaSO_4$, fluorides of trivalent lanthanides, and the like. Additional representitive materials are listed in Chapter 3 of Walton, *The Formation and Properties of Precipitates* (John Wiley and Sons, New York, 1967). Among these representitive materials, the most preferred are those which are insoluble or only slightly soluble in water, which are transparent or substantially transparent to the fluorescent signal and excitation beam, and which have relatively high molecular mass components. Examples of the most preferred materials include $CaF_2$, $LaF_3$, $TbF_3$, $GdF_3$, $SrF_2$, $PbCl_2$, and the like. Nonradiative decay via phonon production competes directly with fluorescence and energy transfer mechanisms which are basic to the invention. The most important parameter in phonon-assisted nonradiative decay rates is the energy gap from the excited ion state to the next lowest level. As the gap decreases the probability for nonradiative relaxation increases. The greater the number of phonons involved in the interaction necessary to bridge the energy gap, the less probable will be a nonradiative transition. Consequently, lattices with lower average phonon energies, which require more phonons to decay to the next lowest energy level, are less competitive with radiative decay mechanisms or energy transfer mechanisms than are lattices with high average phonon energies. Lattices with high molecular weight components vibrate at lower frequencies, and therefore have lower energy phonon spectra. Thus, such lattice materials are preferred over those with lower molecular mass components.

B. Calcination

After coprecipitation, the microcomponent (in this case an actinide ion) is trapped in the microcrystalline structure of the host lattice. Due to the heterogeneous nature of the coprecipitation, the actinide ions and fluorescent component species reside in a variety of sites. Each site possesses slightly different fluorescence characteristics resulting in a broad fluorescence spectrum, or in the case of selective excitation, a lower fluorescent yield per site.

In addition to the actinides of interest and the fluorescent component species, other impurities in the water also coprecipitate out of solution. When these impurities are organic they cause a broad fluorescent background that tends to mask the fluorescence spectrum of the fluorescent component species.

Both of these problems are eliminated by calcination of the precipitate. Heating the precipitate has several effects. First, temperatures above about 500° C. will cause the organics to oxidize and then vaporize. Second, vacancies and interstitials become mobile at these elevated temperatures. The crystals then rearrange themselves into a more homogeneous lower energy configuration. Consequently, when cooled the precipitate possesses no interfering organic impurities and a smaller selection of sites for the actinide and the fluorescent component species. This leads to narrower more intense fluorescence spectrums which are also free of the broadband organic fluorescence background. Calcination temperature is, of course, limited by the melting point of the macrocomponent of the precipitate. Calcination for about 1-3 hours at between about 500° C. and about 1000° C. produces suitable results for $CaF_2$ and $TbF_3$.

In some cases the actinide itself can become oxidized during calcination leading to a different species and therefore a different characteristic fluorescence spectrum. Uranium provides an excellent example of this phenomenon. In natural waters, uranium is found as uranyl, $UO_2^{++}$, complexed with various anions. It can be readily coprecipitated with calcium fluoride. The precipitate then contains a microcomponent consisting of uranyl ions. After calcination the precipitate gives a fluorescence spectrum characteristic of the uranate molecule, $UO_6^{-6}$. Additional oxygen from the air oxidized the $UO_2^{++}$ to $UO_6^{-6}$ during calcination. To avoid such oxidation calcination must be performed in vacuo.

C. Excitation Sources and Fluorescence Analysis

A laser light source operating at a preselected wavelength is used to illuminate the calcined precipitate to excite the actinide or the fluorescent component species to a particular energy level. Whether the actinide quenches or sensitizes the fluorescent component species determines whether the excitation frequency (i.e., the preferred frequency of the laser) is preselected to excite the actinide or the fluorescent component species. If the actinide acts as a sensitizer, then a frequency is chosen to excite the actinide to a level above the near resonant energy level of the fluorescent component species, but close enough to the near resonant level so that non-radiative decay to that level is likely. If the actinide acts as a quenching agent to the fluorescent component species, then a frequency is chosen that corresponds to the near resonant energy level of the fluorescent component species. Use of a tunable dye laser is preferred in order to efficiently and selectively excite either the actinide or the fluorescent component species; however, use of a tunable dye laser is not crucial.

FIG. 1 is a block diagram of one embodiment of apparatus for illuminating a sample and/or standard and for measuring the resulting fluorescent spectra in accordance with the practice of the invention. This apparatus allows measurement of both spectra and fluorescent lifetimes.

For particular actinide-preselected host material combinations less complicated apparatus is adequate. For example, a filter fluorimeter alone may be sufficient for fluorescence analysis once an actinide-fluorescent component species system is chosen.

In FIG. 1 output 4 from laser 2 is passed through interference filter 6, or alternatively through a Claassen prism iris combination, or the like, to filter out all plasma lines while allowing the chosen laser wavelength to pass. The laser beam is steered via aluminum coated mirrors, 14 and 16, to a sample illuminator 18, e.g., Spex model 1430 (Spex Corp., Metuchen, N.J.), or the like. There the laser light is focused to a 20 μm-sized spot on the sample pellet. Collection optics 20 collect and direct the fluorescent light to double monochromator 22, e.g., Spex model 1402 double monochromator, or the like. Light from double monochromator 22 is directed to a photomultiplier tube 24, e.g., RCA model 31034a-02 (RCA Electronic Components, Harrison, N.J.), or the like. The photomultiplier tube is cooled, or the like, e.g., by a Products for Research model TE-104-RF thermo-electric cooler, in order to reduce the tube's dark current. Since the photomultiplier tube is a photon counting device, the signal is processed by fast preamplifier 26, and suitable post amplifier 28, discriminator 30, and rate meter 32, e.g., Ortec series 9300 (Ortec, Inc., Oak Ridge, Tenn.), or the like. The output of the rate meter either drives a chart recorder, e.g., Gould model 110 (Gold, Inc., Santa Clara, Calif.), or the like or is digitized by digital multimeter 36, e.g. Hewlett Packard model 3456 (Hewlett Packard, Palo Alto, Calif.), or the like. The output of the digital multimeter is stored in tabulated form in a microcomputer 38, e.g., Tektronix model 4051 (Tektronix, Inc., Beaverton, Oreg.) in conjunction with a DEC LSI 11/23 (Digital Equipment Corp., Waltham, Mass.), or a similar microcomperized data acquisition system. When a spectrum is completed it is displayed by plotter 40.

In order to make accurate determinations of fluorescent lifetimes and to increase the detection limits by discrimination against impurities possessing relatively fast fluorescence, a boxcar integrator 34 can be utilized, e.g., Princeton Applied Research model 162 (Princeton Applied Research, Princeton, N.J.), or the like. The boxcar replaces the rate meter in the signal processing system.

The boxcar temporally discriminates by (1) receiving a trigger pulse from a repetitive signal; (2) waiting a specified amount of time; then (3) setting up a temporal window during which the boxcar integrates the signal. The output asymptotically approaches the average value of the input signal coincident with the temporal window. The cw laser light is pulsed by a mechanical chopper 8. The chopping rate is monitored by sampling a small portion of the beam via a beasmsplitter 10 and photodiode 12. The photodiode output then acts as a trigger for boxcar 34.

EXAMPLE I

Plutonium Detection

The concentration of plutonium ions, $Pu^{+3}$, is determined indirectly by their quenching effect on terbium fluorescence.

Terbium fluoride is formed and precipitated from water by adding terbium nitrate, $Tb(NO_3)_3$, to ammonium fluoride, $NH_4F$. The reaction is described by the following equation.

$$Tb(NO_3)_3 + 3NH_4F \rightleftharpoons 3NH_4NO_3 + TbF_3$$

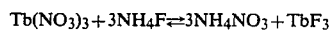

The maximum $TbF_3$ precipitation occurs when terbium ions and fluorine ions are present in stochiometric amounts, in this case, in the ratio of 3 moles of fluorine for every mole of terbium.

Plutonium has the unique ability to have all four common oxidation states coexist in the same solution. This is due to the tendancy of plutonium ions to disproportionate in the presence of water according to the following equation.

$$3Pu^{+4} + 2H_2O \rightleftharpoons 2Pu^{+3} + PuO_2 + 4H^+$$

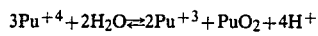

For example, a $10^{-2}$ M solution of $Pu^{+4}$ in 0.344 M $HNO_3$ disproportionates into 12% $Pu^{+3}$, 66% $Pu^{+4}$, and 22% $Pu^{+6}$. Due to such disproportionation, plutonium must be placed in a strong reducing or oxidizing solution in order to prepare it in a particular oxidation state.

The $Pu^{+3}$ form is ensured by mixing the sample with an appropriate amount of $NaHSO_3$. Reduction of $Pu^{+4}$ occurs according to the following equation.

$$2Pu^{+4} + HSO_3^- + Na^+ + H_2O \rightleftharpoons 2Pu^{+3} + SO_4^{-2} + Na^+ + 3H^+$$

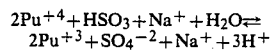

As an example, the dominance of the $Pu^{+3}$ form is ensured by mixing a $5 \times 10^{-3}$ M solution of plutonium with an equal volume of a 0.25 M solution of $NaHSO_3$.

In this example, the host precursor materials are $Tb(NO_3)_3$, $NH_4F$, and $NaHSO_3$.

After terbium nitrate and ammonium fluoride are mixed with the actinide-containing sample, terbium fluoride starts to precipitate immediately and is finished within a period of about two hours. The solution is stirred and placed in a thick-walled centrifuge cone. It is centrifuged for about ten minutes and the supernatant is discarded. The precipitate is washed with about 10 ml of water and centrifuged for an additional 10 minutes. The supernatant is once again discarded and the precipitate is dried under a heat lamp at a temperature of 100° C. for two hours. The precipitate is then removed from the centrifuge tube and placed in an agate mortar where it is ground to a fine powder. The powdered precipitate is then transferred to a quartz tube and a piece of wool is inserted in the neck of the tube to confine the powder. This tube is placed on a vacuum line where no oxygen can interact with the precipitate. A clamshell heater is then placed around the quartz tube. The heater is set at about 100° C. for about one hour. After an hour, the temperature is increased slowly over a period of about one hour to about 800° C. If the temperature is increased too rapidly, the powder begins to swirl violently and a portion of the sample can be lost. The precipitate is calcined for about three hours and then cooled thoroughly. After cooling, the calcined precipitate is pulverized using a pulverizing device such as the one sold under the tradename Wig-1-bug (Spex Corp. Metuchen, N.J.), or the like. 200 mg of pulverized calcined precipitate is placed in a pellet die and pressed for one minute at 10,000 psi. This produces a sample pellet 1 cm in diameter and approximately 1 mm thick that is ready for fluorescence analysis.

The finished pellet is placed between two pieces of quartz, one of which has a recessed space for the pellet. These are epoxied together and set aside for 24 hours.

Figure 2:
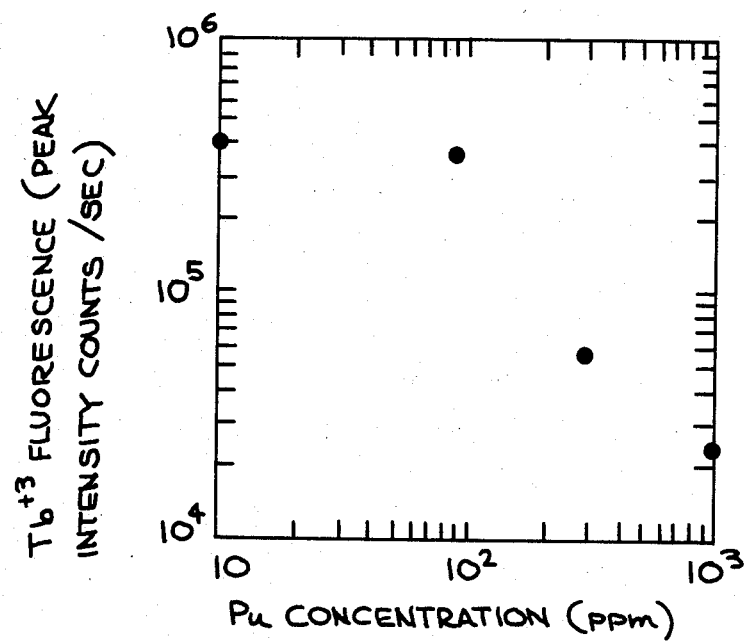
FIG. 2 is a graph showing the degree of terbium fluorescence quenching as a function of plutonium concentration.

FIG. 2 shows the degree of terbium fluorescence quenching as a function of plutonium concentration. These results were obtained by exciting terbium fluorescence with 457.1 nm laser light. This wavelength, which is not crucial, is sufficient for exciting terbium into its $^5D$ energy levels. It is crucial to this example that the preselected wavelength be chosen so that terbium is excited into its $^5D$ energy levels. From these energy levels energy may be transferred to a near resonant energy level, the $^4G_{7/2}$ level, in a nearby plutonium ion.

The concentration of 100 parts per million by weight of $^{242}Pu$ indicates that approximately one terbium ion in 15,000 has been substituted by a plutonium ion. Thus, on the average there are 25 $Tb^{+3}$ ions for every $Pu^{+3}$ ion along any one of the crystalline axes. The onset of quenching of the terbium fluorescence at this concentration implies a significant energy migration among the $Tb^{+3}$ ions to allow the $Pu^{+3}$ ions to accept the energy from either their nearest or next nearest neighbors, the largest separation for which the dipole—dipole interaction (the dominant $Pu^{+3}$-$Tb^{+3}$ energy transfer mechanism) remains competitive with radiative processes.

For the results in FIG. 2, 15 ml of 0.1 M $Tb(NO_3)_3$ is added to a 5 ml sample. This, in turn, is combined with 50 ml of 0.3 M $NH_4F$.

For use with samples of unknown composition, The fluorescent output of the coprecipitate prepared with the unknown sample is compared to that of a standard, in this case an identically prepared sample with known $Pu^{+3}$ concentration.

EXAMPLE II

Americium Detection

Concentrations of americium ion, $Am^{+3}$, are determined indirectly by their sensitizing effect on terbium fluorescence.

Sample preparation procedure follows that of the plutonium samples except that no reduction step is required since americium has no tendancy to disproportionate.

A laser frequency is chosen to excite the $Am^{+3}$ ions preferentially to their $^5D$ levels. An energy transfer then takes place from the $^5D$ states of $Am^{+3}$ ion to the near resonant $^5D_4$ level of $Tb^{+3}$ ions via electric dipole interaction. The $Tb^{+3}$ ion then decays radiatively, thus enhancing or sensitizing the overall $Tb^{+3}$ ion fluorescence.

Figure 3:
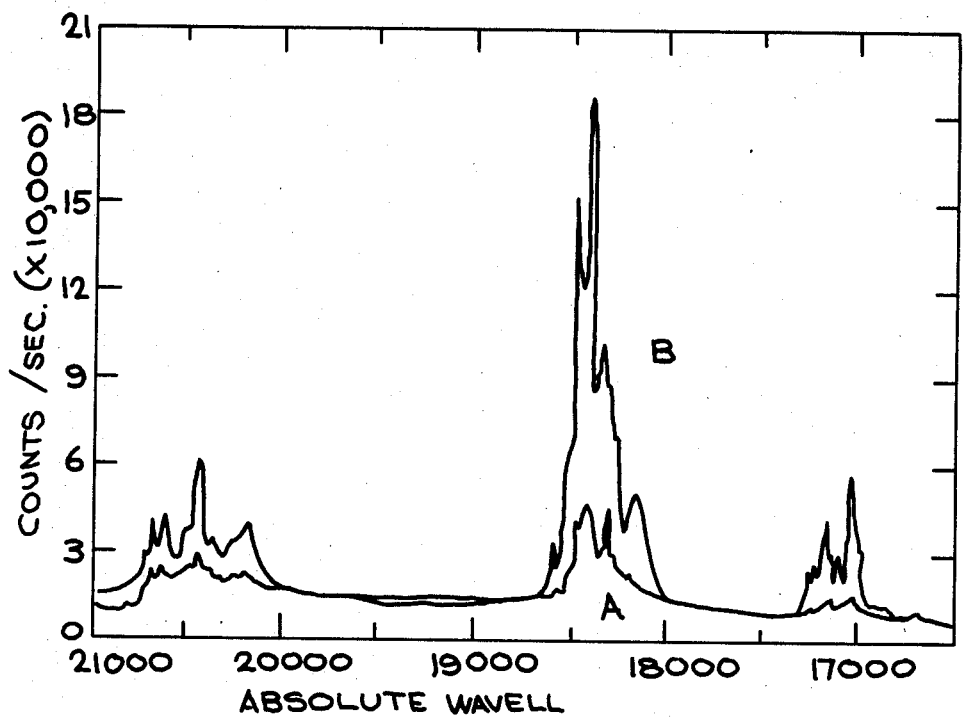
FIG. 3 is a graph showing terbium ion fluorescence spectra with and without sensitization by americium.

FIG. 3 shows the degree of terbium fluorescence enhancement due to americium sensitization. Curve A is the fluorescent spectrum without americium; curve B is the fluorescent spectrum with americium. Here the concentration of $Am^{+3}$ is 1 ppm, and the precipitate is excited by 457.1 nm laser light.

EXAMPLE III

Americium Detection

Here concentrations of americium ion, $Am^{+3}$, are determined indirectly by their sensitizing effect on europium, which is present as an impurity in a calcium fluoride matrix.

The calcium fluoride host lattice with europium, $Eu^{+3}$, as an impurity (1-2%) is formed and precipitated from water by adding amnonium fluoride, $NH_4F$, to a solution of calcium nitrate, $Ca(NO_3)_2$ which contains the unknown sample and europium ions, such that $Eu^{+3}$ comprise about 2% of the cations present (europium is added in the form of europium chloride, $EuCl_3$, or europium nitrate, $Eu(NO_3)_3$). For example, 15 ml of 0.1 M $Ca(NO_3)_2$ and 0.002 M $Eu(NO_3)_3$ is added to a 5 ml actinide-containing sample. This is then combined with 30 ml of 0.3 M $NH_4F$. Coprecipitation, calcination and preparation of the coprecipitate for fluorescent analysis proceeds as in the case for plutonium detection. The americium in the coprecipitate is preferentially excited to the $^5D$ levels by 457.1 nm laser light. Energy transfer occurs between the $^5D$ levels of americium to the $^5D$ levels in europium. Americium concentration is determined by comparing the degree of europium fluorescence enhancement over an identically prepared standard containing the same concentration of europium.

The descriptions of the foregoing examples of the invention has been presented for purposes of illustration and description. They are not intended to be exhaustive or to limit the invention to the precise form disclosed, and obviously many modifications and variations are possible in light of the above teaching. The examples were chosen and described in order to best explain the principles of the invention and its practical application to thereby enable others skilled in the art to best utilize the invention in various contexts and with various modifications as are suited to the particular use contemplated. It is intended that the scope of the invention be defined by the claims appended hereto.

I claim:

1. A method for detecting ultratrace quantities of weakly or non-fluorescing transuranic actinides in water, the method comprising the steps of:
   (a) coreciptating an actinide in a water sample with host precursor materials to form a precipitate, the precipitate comprising a preselected host material which includes at least one fluorescent component species having a near resonant energy level with the actinide and whose fluorescence is quenched or sensitized by the actinide;
   (b) illuminating the precipitate with laser light of a preselected wavelength, said wavelength being selected in the case of sensitizing by the actinide to excite the actinide to a level above and sufficiently close to the near resonant energy level of the at least one fluorescent component species to cause substantial nonradiative decay from the actinide to the near resonant energy level, said wavelength being selected in the case of quenching by the actinide to excite the at least one fluorescent component species to the near resonant energy level, so that the at least one fluoroescent component species is caused to fluoresce and energy is transferred between the near resonant energy level of the at least one fluorescent component species and the actinide;

(c) measuring a difference in intensity between the fluorescence of the at least one fluorescent component species which has been quenched or sensitized by the actinide from the sample and the fluorescence of the at least one fluorescent component species in at least one standard, said at least one standard having been prepared with a known concentration of the actinide; and (d) determining the concentration of the actinide in the sample by relating the difference in the fluorescence intensity to quantitative differences between the concentration of the actinide in the sample and the concentrations of the actinide in said at least one standard.

2. The method as recited in claim 1 wherein said preselected host material includes a host lattice material comprising an ionic crystalline solid.

3. The method as recited in claim 2 wherein the method further comprises, after said step of copreciptating, the step of calcining said precipitate at a temperature above about 500° C. and below the melting point of said preselected host material to form a calcined precipitate.

4. The method as recited in claim 3 wherein said preselected host material further includes said at least one fluorescent component species and wherein said at least one fluorescent component species is selected from the group consisting of the fluorescent lanthanides, the fluorescent transition metals, and uranyl.

5. The method as recited in claim 4 wherein said actinide quenches fluorescence of said at least one fluorescent component species and said step of coprecipitating further includes providing said at least one fluorescent component species having the near resonant energy level with said actinide such that whenever electrons in said at least one fluorescent species are excited to said near resonant energy level, energy is transferred component to said actinide.

6. The method as recited in claim 5 wherein said host lattice material is an ionic crystalline solid with a melting point above about 500° C.

7. The method as recited in claim 6 wherein said host lattice material is insoluble or slightly soluble in water, has a low energy phonon spectra, and is substantially transparent to fluorescent emissions from said at least one fluorescent component species and to light of said preselected wavelength.

8. The method as recited in claim 7 wherein said host lattice material is selected from the group consisting of $CaF_2$, $LaF_3$, $TbF_3$, $GdF_3$, $SrF_2$, and $PbCl_2$.

9. The method as recited in claim 8 wherein said actinide being detected is plutonium,
  (a) said step of coprecipitating includes providing terbium fluoride as said host lattice material;
  (b) said step of calcining said precipitate includes maintaining said precipitate at a temperature within the range of about 500° C. to 1000° C.;
  (c) said step of illuminating the calcined precipitate includes selecting said preselected wavelength so that terbium within the calcined precipitate is excited to its $^5D$ energy levels;
  (d) said step of measuring includes measuring the difference between the intensity of terbium fluorescence in the calcined precipitate containing plutonium from said sample and the intensity of terbium fluorescence in said at least one standard; and
  (e) said step of determining includes determining the concentration of plutonium in said sample by relating the difference in terbium fluorescence intensity to quantitative differences between the concentration of plutonium in said sample and the concentrations of plutonium in said at least one standard.

10. The method as recited in claim 9 wherein said step of calcining further comprises raising the temperature of said precipitate uniformly from room temperature to about 800° C. over a period of about one hour, and maintaining said precipitate at about 800° C. for about three hours.

11. The method as recited in claim 9 wherein said host precursor materials comprise terbium nitrate, ammonium fluoride, and sodium sulfate hydrogen.

12. The method as recited in claim 4 wherein said actinide in said sample sensitizes said at least one fluorescent component species and said step of coprecipitating further includes providing said at least one fluorescent component species which possesses the near resonant energy level with said actinide such that said actinide possesses an energy level higher than the near resonant energy level, the higher level being absent in said fluorescent component species and the higher level having the property that whenever electrons in said actinide are excited to the higher level they decay to the near resonant energy level in a predominantly nonradiative manner.

13. The method as recited in claim 12 wherein said host lattice material is an ionic crystalline solid with a melting point above about 500° C.

14. The method as recited in claim 13 wherein said host lattice material is insoluble or slightly soluble in water, has a low energy phonon spectra, and is substantially transparent to fluorescent emissions from said at least one fluorescent component species and to light of said preselected wavelength.

15. The method as recited in claim 14 wherein said host lattice material is selected from the group consisting of $CaF_2$, $LaF_3$, $TbF_3$, $GdF_3$, $SrF_2$, and $PbCl_2$.

16. The method as recited in claim 15 wherein said actinide is americium and said preselected host material comprises calcium fluoride and said at least one fluorescent component species comprises trivalent europium.

17. The method as recited in claim 15 wherein said actinide being detected is americium,
  (a) said step of coprecipitating includes providing terbium fluoride as said host lattice material;
  (b) said step of calcining said precipitate includes maintaining said precipitate at a temperature within the range of about 500° C. to 1000° C. for about 1–3 hours;
  (c) said step of illuminating the calcined preciptate includes selecting said preselected wavelength so that americium within the calcined precipitate is excited to its $^5D$ energy levels;
  (d) said step of measuring includes measuring the difference between the intensity of terbium fluorescence in the calcined precipitate containing americium from the sample and the intensity of terbium fluorescence in said at least one standard, said at least one standard having been prepared with a known concentration of americium; and (e) said step of determining includes determining the concentration of americium in said sample by relating the difference in terbium fluorescence intensity to quantitative differences between the concentration of americium in said sample and the concentrations of americium in said at least one standard.

18. The method as recited in claim 17 wherein said host precursor materials comprise terbium nitrate and ammonium fluoride.

* * * * *